United States Patent [19]  
Birum et al.

[11] 3,968,188  
[45] July 6, 1976

[54] PROCESS FOR PREPARING THE PENTAERYTHRITOL ESTER OF PHOSPHOROHALIDOUS ACID

[75] Inventors: Gail H. Birum; Michael L. Losee, both of Kirkwood, Mo.

[73] Assignee: Monsanto Company, St. Louis, Mo.

[22] Filed: Feb. 4, 1974

[21] Appl. No.: 439,504

[52] U.S. Cl. .............................. 260/976; 260/927 R
[51] Int. Cl.$^2$ .......................................... C07F 9/15
[58] Field of Search ................................... 260/976

[56] References Cited
UNITED STATES PATENTS

| | | | |
|---|---|---|---|
| 2,220,845 | 11/1940 | Moyle | 260/976 X |
| 3,042,697 | 7/1962 | Halter et al. | 260/976 X |
| 3,192,242 | 6/1965 | Birum | 260/976 X |
| 3,415,907 | 12/1968 | Sconce et al. | 260/976 X |
| 3,519,607 | 7/1970 | Welch | 260/973 X |
| 3,689,602 | 9/1972 | Ismail | 260/976 X |

*Primary Examiner*—Anton H. Sutto
*Attorney, Agent, or Firm*—Robert E. Wexler

[57] ABSTRACT

The pentaerythritol ester of phosphorohalidous acid is prepared by reacting pentaerythritol and a trivalent phosphorus trihalide in the presence of a catalyst. The pentaerythritol ester of phosphorohalidous acid is a useful intermediate in the preparation of halogenated organophosphate flame retardant materials.

12 Claims, No Drawings

PROCESS FOR PREPARING THE PENTAERYTHRITOL ESTER OF PHOSPHOROHALIDOUS ACID

PRIOR ART RELATING TO THE PRESENT INVENTION

U.s. Pat. No. 3,192,242 describes the preparation of the pentaerythritol ester of phosphorohalidous acid and describes the use of such compound as an intermediate in the preparation of 2,2-bis(halomethyl)-1,3-propylenebis(phosporodihalidates) and halogenated diphosphate esters thereof.

In accordance with the teachings of the patent, the pentaerythritol ester of phosphorohalidous acid (3,9-dichloro-2,4,8,10-tetraoxa-3,9-diphosphospiro[5.-5]undecane, "DDS") is prepared by the reaction of pentaerythritol and a trivalent phosphorus trihalide. As taught by the patent, the pentaerythritol and trivalent phosphorus trihalide are reacted at a mole ratio of pentaerythritol to trivalent phosphorus trihalide of 1:1 ⅓ to 1:2, preferably using a 2 to 25 mole percent excess of phosphorus trihalide. The reaction is conducted at a temperature of about 80°C. for approximately 3 and ½ hours.

It is disclosed in the patent that side-reaction products, for example, products having phosphorus-containing groups such as in the following structure:

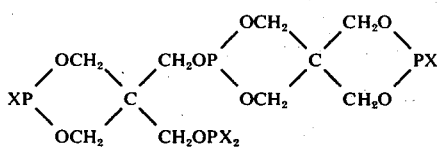

wherein X represents halogen, are formed during the pentaerythritol/phosphorus trihalide reaction and it is further taught that such side reaction products may be eliminated by purification of the pentaerythritol ester of phosphorohalidous acid. It is still further taught, however, that it was preferred to retain such side reaction products since they did not appear to appreciably degrade the properties of the final product.

BACKGROUND OF THE INVENTION

In addition to the phosphorus-containing groups of side-reaction products described in U.S. Pat. No. 3,192,242, it has been found that the following phosphorus-containing group is also formed:

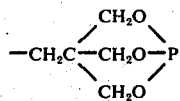

For example, the following compound has been specifically identified:

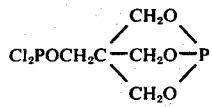

In the reaction of the pentaerythritol ester of phosphorohalidous acid to produce flame retardant materials, i.e. by the subsequent reaction of the pentaerythritol ester of phosphorohalidous acid with halogen and, if desired, epoxy compounds as disclosed in U.S. Pat. No. 3,192,242, it has been discovered that such flame retardant materials are of inferior quality due to variations in the viscosity of the products obtained and because of a variation in the concentration of low boiling components, formed from the side-reaction products, contained therein. In order to function properly as a flame retardant, the flame retardant product must be of relatively constant viscosity and contain as low a concentration as possible of low boiling components. Further, it has become clear that purification of the pentaerythritol ester of phosphorohalidous acid, prior to subsequent reactions to produce a flame retardant, lowers the yield, thereby raising the cost, and does not conveniently eliminate the viscosity and low boiling component variations of subsequent reaction products.

SUMMARY OF THE INVENTION

In accordance with the present invention, it has been found that the use of certain catalysts in the reaction of pentaerythritol with a trivalent phosphorus trihalide results in the formation of substantially pure DDS. It was found, for example, that if crude DDS material, which upon subsequent reaction afforded final products of inferior quality because of the low boiling components and viscosity variation, was allowed to stand for a few days, much of the side-reaction products responsible for inferior quality rearranged to DDS and that subsequent reaction products prepared from such DDS material, which had been allowed to stand for a number of days, had improved quality. Since allowing DDS material to stand for a number of days to allow the side-reaction products to rearrange themselves into DDS was time consuming and expensive, an alternate method was sought to obtain the same result in a shorter, practical period of time.

Accordingly, it has now been found that the use of certain catalysts directs the rearrangement of side-reaction products to DDS and reduces the time necessary for such rearrangement.

DESCRIPTION OF THE PREFERRED EMBODIMENTS

In accordance with the present invention it has been found that substantially pure DDS is obtained by reacting pentaerythritol with a trivalent phosphorus trihalide in the presence of halides of metals of Groups I and II of the Periodic Table, tertiary amines and heterocyclic nitrogen-containing compounds.

In particular, it has been found that the halides of lithium, sodium, potassium, calcium, beryllium, copper, zinc, silver, cadmium and magnesium catalyze the rearrangement of side-reaction products to DDS. Preferably, lithium chloride, sodium chloride, potassium chloride, calcium chloride and magnesium chloride are used in accordance with the method of this invention.

Further, it has been found that tertiary amines of the formula:

wherein R represents an alkyl group of from 1 to 12 carbon atoms and/or an aryl group of from 6 to 12 carbon atoms, and wherein R may be optionally substituted with groups which do not contain a reactive hydrogen atom, will catalyze the rearrangement of side reaction products to DDS. Specific groups represented by R include methyl, ethyl, propyl, butyl, amyl, hexyl, heptyl, octyl, nonyl, decyl, undecyl, dodecyl, ethylhexyl, isopropyl, phenyl, naphthyl and the like.

Optional groups with which R may be substituted include nitro, chloro, alkyl, cyano and the like. Reactive hydrogen-containing groups with which R may not be substituted include hydroxyl, primary amino, secondary amino, thiol, carboxyl and the like.

Specific tetriary amines which are useful as catalysts in accordance with the present invention include dimethylaniline, diethylaniline, dipropylaniline, dibutylaniline, diamylaniline, dihexylaniline, diheptylaniline, dioctylaniline, didecylaniline, methylethylaniline, ethylpropylaniline, p-nitro-dimethylaniline, p-diethylaniline, trimethylamine, triethylamine, tripropylamine, dimethyl naphthylamine, and similar compounds.

Still further it has been found that heterocyclic nitrogen compounds of the formula

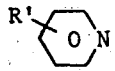

wherein R' represents hydrogen or an alkyl group of 1-5 carbon atoms, e.g. methyl, ethyl, propyl, butyl, amyl and salts thereof, e.g. hydrochlorides and hydrobromides, catalyze the rearrangement of side reaction products to DDS.

Specific heterocyclic nitrogen compounds which are useful as catalysts include pyridine, 2-, 3- and 4-methylpyridine, 2-, 3- and 4-ethylpyridine, 3-propylpyridine and 4-butylpyridine and salts thereof, e.g. hydrochlorides.

The catalyst is used in a concentration of from about 0.005 percent to about 2 percent (based on pentaerythritol), preferably from about 0.05 to about 1 percent by weight.

The trivalent phosphorus trihalides which are normally used in the process of this invention are phosphorus trichloride and phosphorus tribromide. The preferred mole ratio of the phosphorus trihalide to pentaerythritol required to produce DDS is 2:1. As a practical matter, slight variations from that ratio are acceptable.

An excess of phosphorus trichloride may be charged initially to make up for losses caused by entrainment with hydrogen chloride during the reaction. Less than the needed amount of phosphorus trichloride, however, may be charged and after elimination of hydrogen chloride is essentially complete, the additional amount of phosphorus trichloride needed to provide the 2:1 molar ratio may be added. The mixture is then warmed until the rearrangement of undesired structures to DDS is essentially complete. Additional pentaerythritol may, similarly, be added toward the end of the reaction when needed to compensate for initial deficiencies of this reactant. Thus, undesired phosphorus-containing structures that result from a deficiency of either reactant can be readily converted to the desired DDS structure by adding enough of the deficient reactant to bring the molar ratio of reactants consumed to 2:1 and then warming in the presence of a catalyst described above.

The reactants are usually mixed at a temperatuare of from about 20° to about 30°C. and then gradually warmed. A temperature of from about 80°C. to about 125°C. for from about ½ to about 2 hours in the presence of an aforedescribed catalyst is generally required to complete the reaction. Preferably, the reaction is heated to a temperature of from about 90° to about 115°C. and held for ½ to about 2 hours.

The catalyst may be added when the reactants are initially mixed or may be added after the temperature of the reaction mixture has reached about 80°C. or above to promote rearrangement of undesired structures to DDS.

As set forth in U.S. Pat. No. 3,192,242, the pentaerythritol ester of phosphorohalidous acid is a useful intermediate in the preparation of 2,2-bis(halomethyl)-1,3-propylenebis(phosphorodihalidates) and halogenated diphosphate esters thereof. As set forth in the described patent, the reaction of DDS with halogen produces compounds having the structure (I) as set forth in said patent and further reaction of said compound of structure (I) with an epoxy compound afford halogenated diphosphate esters as exemplified by the compounds of structure (II) of said patent.

Compounds having the structure (I) of U.S. Pat. No. 3,192,242, which are obtained by halogenating DDS, include 2,2-bis-(chloromethyl)-1,3-propylenebis(phosphorodichloridate), 2,2-bis(chloromethyl)-1,3-propylenebis(phosphorobromidochloridate), 2,2-bis(bromomethyl)-1,3-propylenebis(phosphorodibromidate) and similar compounds.

It is the compounds of structure (II) which are most affected with regard to viscosity and low boiling component concentration variations as a result of the reaction of pentaerythritol and a trivalent phosphorus trihalide in the absence of a catalyst.

As set forth in the said patent, certain halogenated diphosphate esters may also be polymerized as set forth therein to obtain polymeric compounds also useful as flame retardants. Among the many halogenated diphosphate esters disclosed in said patent there are included 2,2-bis(bromomethyl)-1,3-propylenebis(2-bromo-3-methacryloxypropyl 2-chloropropyl phosphate), 2,2-bis(chloromethyl)-1,3-propylenebis(2-chloro-3-allyloxypropyl 2-chloroethyl phosphate), 2,2-bis(bromomethyl)-1,3-propylenebis (2-bromoethyl 2-chloroethyl phosphate), 2,2-bis(chloromethyl-1,3-propylenebis[bis(2-chloro-1-methylpropyl) phosphate], and 2,2-bis(chloromethyl)-1,3-propylenebis[bis(2,3-dichloropropyl) phosphate].

U.S. Pat. No. 3,192,242, which is herein incorporated by reference, disclosed that the compounds prepared as described above are useful in various ways. For example, the compounds of structure (I) in U.S. Pat. No. 3,192,242 may be used in the preparation of esters therefrom by reaction with alcohols or mercaptans or may be used in the preparation of phosphoramides by reaction with amines. Further, such materials may be used to treat cellulosics and other substances having multiple hydroxy groups to obtain materials generally imparting flame-proofing properties thereto. Further, it is therein disclosed that the further reaction of the compounds of structure (I) with epoxy compounds afford halogenated diphosphate esters which are useful for a variety of industrial purposes, e.g. as preignition-inhibiting agents in organolead-containing hydrocarbon fuels, as antioxidants, antiwear, and extreme pressure-impartng additives to hydrocarbon lubricant oil based compositions. Further, they are particularly useful as flame retardant materials for natural and synthetic polymers.

The invention is further illustrated by, but not limited to, the following examples:

EXAMPLE 1

A 2-1. flask equipped with a dry ice-cooled condenser is charged with 272 g. (2.0 moles) of pentaerythritol, 569 g. (4.14 moles) of phosphorus trichloride, and 135 g. of chlorobenzene at 25°C. This mixture is stirred and gradually warmed to 105°C. in 2.5 hours and kept at 103°–105° for 1 hour more. A phosphorus nuclear magnetic resonance ($P^{31}$ nmr) spectrum of the resulting reaction mixture contains peaks for five different phosphorus environments: −219 ppm (relative to $H_3PO_4$ at 0.0 ppm) for $PCl_3$, −181 ppm for the $-CH_2OPCl_2$ group, −125 ppm for the $>C(CH_2O)_2\cdot POCH_2$-group, −93 ppm for the $-C(CH_2O)_3P$ group, and −149 ppm for the desired DDS structure.

Anhydrous magnesium chloride powder (2.7 g) is then added to the reaction mixture, and warming is continued at 104-105° for fifty minutes. A $P^{31}$ nmr spectrum of this reaction mixture contains only 1 detectable peak, −149 ppm for DDS.

When the reaction is repeated under similar conditions, except that lithium chloride, potassium chloride or calcium chloride are used in place of magnesium chloride as the catalyst, the crude reaction mixture also has a single $P^{31}$ nmr peak, −149 ppm for DDS.

EXAMPLE 2

A 2-1. flask equipped with a dry ice-cooled condenser is charged with 272 g. (2.0 moles) of pentaerythritol, 495 g. (3.6 moles) of phosphorus trichloride, 2.7 g. of anhydrous magnesium chloride powder, and 194 g. of chlorobenzene solvent at 26°C. After this mixture is stirred and warmed to 100°C. in 2.5 hours, its $P^{31}$ nmr spectrum contains three peaks: −93 ppm for $-C(CH_2O)_3P$, −125 ppm for $>C(CH_2POCH_2-$, and −149 ppm for DDS. Additional phosphorus trichloride, 77 g., the amount needed to make a total of 4.0 moles after accounting for loss of about 0.16 mole by entrainment with hydrogen chloride, is added at 99°–100°C. in four minutes. After further warming at 100°–106°C. for one hour, the reaction mixture has a single detectable $P^{31}$ nmr peak at −149 ppm for the desired DDS.

EXAMPLE 3

A 2-1. flask equipped with a dry ice-cooled condenser is charged with 272 g. (2.0 moles) of pentaerythritol, 0.1 g. of pyridine, and 270 g. of o-dichlorobenzene. Then phosphorus trichloride, 522 g. (3.8 moles), is added dropwise in 16 minutes at 22°–25°C. After this mixture is stirred and warmed to 105°C. in 3.1 hours, its $P^{31}$ nmr spectrum contains three peaks: −94 ppm for $-C(CH_2O)_3P$, −126 ppm for $C(CH_2O)_2\cdot POCH_2-$, and −150 for DDS. An additional 45 g. of phosphorus trichloride, making a total of 4.0 moles after allowing for a loss of about 3% by entrainment by hydrogen chloride, is added below the surface in 3 minutes at 99°–100°C. After this reaction mixture is warmed at 100°–107° for 1 hour more, its $P^{31}$ nmr spectrum contains a single peak, −149 ppm for DDS.

Using about the same conditions, except that pyridine hydrochloride, dimethylaniline or dimethyl p-nitro-aniline is used as the catalyst and all of the required phosphorus trichloride is charged at one time at 25°, likewise gives a product having only a single $P^{31}$ nmr which represents the desired DDS structure.

What is claimed is:

1. In a process for the preparation of the pentaerythritol ester of phosphorohalidous acid by the reaction of pentaerythritol and a trivalent phosphorus trihalide selected from the group consisting of phosphorus trichloride and phosphorus tribromide, the improvement comprising conducting the reaction at a pentaerythritol:phosphorus trihalide molar ratio of 1:2 in the presence of a catalyst selected from the group consisting of (1) lithium chloride, sodium chloride, potassum chloride, calcium chloride and magnesium chloride, (2) a tertiary amine of the formula

wherein R represents an alkyl group of from 1 to about 12 carbon atoms or an aryl group of from 6 to 12 carbon atoms or (3) a heterocyclic nitrogen-containing compound of the formula

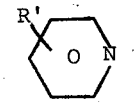

wherein R' represents hydrogen or an alkyl group of 1 to 5 carbon atoms and the hydrochloride or hydrobromide salts thereof.

2. The process of claim 1 wherein said catalyst is lithium chloride.

3. The process of claim 1 wherein said catalyst is magnesium chloride.

4. The process of claim 1 wherein said catalyst is a tertiary amine of the formula

wherein R represents an alkyl group of from 1 to about 12 carbon atoms, an aryl group of from 6 to 12 carbon atoms and mixtures thereof and wherein R may be optionally substituted with groups which do not contain a reactive hydrogen atom.

5. The process of claim 1 wherein said catalyst is a heterocyclic nitrogen-containing compound of the formula

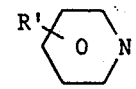

wherein R' represents an alkyl group of from 1 to about 5 carbon atoms, and hydrochloride and hydrobromide salts thereof.

6. In a process for the preparation of 3,9-dichloro-2,4,8,10-tetraoxa-3,9-diphosphospiro undecane by the reaction of pentaerythritol and a trivalent phosphorus trihalide selected from the group consisting of phosphorus trichloride and phosphorus tribromide, the improvement comprising conductng said reaction (a) at a pentaerythritol: phosphorus trihalide molar ratio of 1:2

(b) at a temperature of from about 80° to about 125°C. and (c) in the presence of magnesium chloride as catalyst.

7. The process of claim 6 wherein said pentaerythritol and phosphorus trihalide are initially combined at a temperature of from about 20° to about 30°C.

8. The process of claim 6 wherein a molar excess of phosphorus trihalide is initially charged.

9. The process of claim 6 wherein a molar deficiency of phosphorus trihalide is initially charged.

10. The process of claim 9 wherein sufficient phosphorus trihalide is subsequently charged to adjust the total molar ratio to about 1:2.

11. The process of claim 6 wherein a molar deficiency of pentaerythritol is initially charged.

12. The process of claim 11 wherein sufficient pentaerythritol is subsequently charged to adjust the total molar ratio to about 1:2.

* * * * *

UNITED STATES PATENT OFFICE
CERTIFICATE OF CORRECTION

PATENT NO. : 3,968,188
DATED : July 6, 1976
INVENTOR(S) : Gail H. Birum & Michael L. Losee It is certified that error appears in the above-identified patent and that said Letters Patent are hereby corrected as shown below:

Column 2, line 66, after "to" there should be added the word -- about --.

Column 3, line 13, "tetriary" should be corrected to read -- tertiary --.

Column 4, line 29, after "1,3-propylenebis" there should be added -- (phosphorobromidochloridate), 2,2-bis(bromomethyl)-1,3-propylenebis --.

Column 5, line 40, the formula " $>C(CH_2POCH_2-$ " should be corrected to read -- $>C(CH_2O)_2POCH_2$ --.

Column 6, line 12, "potassum" should be corrected to read -- potassium --.

Signed and Sealed this

Fifth Day of October 1976

[SEAL]

Attest:

RUTH C. MASON
Attesting Officer

C. MARSHALL DANN
Commissioner of Patents and Trademarks